(12) United States Patent
Kropac et al.

(10) Patent No.: US 8,262,927 B2
(45) Date of Patent: Sep. 11, 2012

(54) PROCESS FOR WORKUP OF GLYCOL-CONTAINING AIRCRAFT DEICERS

(75) Inventors: Bernhard Kropac, Kastl (DE);
Wolfgang Kerbl, Englsberg (DE); Erich Gatter, Kastl (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 13/141,902

(22) PCT Filed: Dec. 2, 2009

(86) PCT No.: PCT/EP2009/008583
§ 371 (c)(1),
(2), (4) Date: Aug. 4, 2011

(87) PCT Pub. No.: WO2010/072311
PCT Pub. Date: Jul. 1, 2010

(65) Prior Publication Data
US 2011/0303870 A1    Dec. 15, 2011

(30) Foreign Application Priority Data
Dec. 24, 2008    (DE) .................... 10 2008 063 094

(51) Int. Cl.
*C09K 3/18*    (2006.01)
*B09B 3/00*    (2006.01)
*B64F 5/00*    (2006.01)
*C07C 29/88*   (2006.01)

(52) U.S. Cl. ............ 252/70; 106/13; 210/634; 210/639; 210/644; 210/650

(58) Field of Classification Search ............... 106/13; 252/70; 210/634, 639, 644, 650
See application file for complete search history.

(56) References Cited

U.S. PATENT DOCUMENTS

| 5,411,668 | A | * | 5/1995 | Pollmann et al. ............. 210/638 |
| 5,535,877 | A | * | 7/1996 | Eastcott et al. ................. 203/18 |
| 5,863,973 | A | * | 1/1999 | Carder et al. ................. 524/388 |
| 5,904,321 | A | * | 5/1999 | Cox et al. ................. 244/134 R |
| 6,565,753 | B1 | * | 5/2003 | Holmgren et al. ............ 210/664 |
| 7,713,319 | B2 | * | 5/2010 | Radhakrishnan et al. ... 48/198.7 |
| 2011/0263909 | A1 | * | 10/2011 | Stankowiak et al. ......... 568/868 |

FOREIGN PATENT DOCUMENTS

| CA | 2116827 A1 | * | 5/1995 |
| DE | 19650682 A1 | * | 6/1998 |
| EP | 820793 A2 | * | 1/1998 |

OTHER PUBLICATIONS

Derwent-Acc-No. 2004-255799, abstract of South African Patent Specification No. SE200200606A (Aug. 2003).*

* cited by examiner

*Primary Examiner* — Anthony J Green
(74) *Attorney, Agent, or Firm* — Tod A. Waldrop

(57) ABSTRACT

The invention provides a process for working up glycol-containing aircraft deicers, by (1) removing the suspended impurities from the used aircraft deicer, (2) treating the product thus obtained in such a way that the thickeners present therein are no longer capable of gel formation, (3) before or after step (2) establishing a pH of >7, (4) and then fractionally distilling off the glycols.

5 Claims, No Drawings

PROCESS FOR WORKUP OF GLYCOL-CONTAINING AIRCRAFT DEICERS

The invention relates to a method for reprocessing used aircraft de-icing agents based on glycols.

Aircraft de-icing agents based on glycols are described for example in U.S. Pat. Nos. 4,358,389 and 4,744,913. They generally comprise
(a) about 40 to 80% by weight of at least one glycol having 2 or 3 carbon atoms or of a diglycol having 4 to 6 carbon atoms, for example ethylene glycol, diethylene glycol, propylene glycol and the like,
(b) 0.05 to 1.5% by weight of at least one polymeric component as thickener, for example from the group of polyacrylates, polymethacrylates, xanthan gum and cellulose derivatives,
(c) 0.05 to 1% by weight of at least one surfactant, for example olefinsulfonates, alkylarylsulfonates, polyoxalkylates and the like,
(d) at least one corrosion inhibitor in an effective amount, for example from the group of triazoles, imidazoles and/or phosphoric acid esters, and
(e) at least one basic compound for adjusting the pH to from about 7.5 to 11 and
(f) water as remainder to 100% by weight.

These aircraft de-icing agents are applied to the parts of the aircraft to be treated as they are (i.e. as concentrate) or following dilution with water for their preservation and/or for the freeing of ice and/or snow. The de-icing agent, which is now more or less diluted with melt water and contaminated with sand, rubber dust, oil, combustion residues and the like, flows from the treated parts of the aircraft into a collecting vessel and is referred to as wastewater from the aircraft de-icing or as used aircraft de-icing agent.

The used aircraft de-icing agents are sometimes disposed of with the help of a biological wastewater treatment plant. However—despite the good biodegradability of glycols—this leads to an undesired burden on the wastewater treatment plant, especially at low outside temperatures and reduced bacteria activity associated therewith, which is generally the case when using de-icing agents. A further disadvantage of this type of disposal of aircraft de-icing agents is the loss of the large amount of valuable glycol.

EP-A-0 637 620 discloses a method for reprocessing used aircraft dicing agents based on glycol, in which
(1) the used aircraft de-icing agent is firstly filtered to separate off the suspended impurities,
(2) the filtrate obtained in step (1) is subjected to an ultrafiltration to separate off the polymeric thickeners,
(3) the permeate obtained in step (2) is subjected to ultrafiltration with an anion exchanger and a cation exchanger to separate off any salts and ionic compounds present, and
(4) the solution obtained in step (3) is distilled to the desired value to remove excess water and thus adjust the glycol content, and
(5) the glycol/water mixture obtained is supplied with suitable additives for use as aircraft de-icing agent.

EP-A-1 889 658 discloses a method for reprocessing glycol-containing aircraft de-icing agents in which they are subjected directly to a separation by means of a membrane, thus excluding a distillation in a subsequent method step.

It has now been observed that the de-icing agents reprocessed according to the prior art still contain considerable fractions of organic acids and their glycol esters, and also other impurities after a number of recycling steps. These bring about reduced long-term stability of new thickened deicers which have been produced using de-icing agent constituents reprocessed in such a way. This problem cannot be solved by a simple distillation of the used de-icing agents since, during distillation, the thickener present in the de-icing agent produces a gel which blocks the distillation device.

The object of the invention is accordingly to propose a simple and cost-effective method which makes it possible to largely recover and reuse in particular the glycols from used aircraft de-icing agents, and where the reusability of the glycols is retained.

The present invention therefore provides a method for reprocessing aircraft de-icing agents comprising glycol, in which
(1) the suspended impurities are separated off from the used aircraft de-icing agent,
(2) the product obtained in this way is treated such that the thickeners present therein are no longer capable of gel formation,
(3) before or after step (2), a pH>7 is established,
(4) and then the glycols are fractionally distilled off.

In a preferred embodiment, the glycols are glycols having 2 or 3 carbon atoms or diglycols having 4 to 6 carbon atoms, for example ethylene glycol, diethylene glycol or propylene glycol. Particular preference is given to propylene glycol and monoethylene glycol.

Preferably, in a first step, the constituents present in undissolved form are filtered off. These are, for example, solids such as sand and rubber dust, also suspended matter, oil particles and the like. For this coarse filtration, which is preferably carried out at room temperature and atmospheric pressure, it is possible to use the customary filter materials, for example paper, cloth, fabric and the like.

Prevention of gel formation by the thickeners present in the used aircraft de-icing agent can take place in various ways.

In a first preferred embodiment, the filtrate obtained by the coarse filtration can be subjected to an ultrafiltration through a membrane, such that the polymeric thickener is separated off. In addition, emulsified oil, higher hydrocarbons, surfactants and the like which may for example be present are also separated off to a greater or lesser extent. The ultrafiltration step is preferably carried out using an ultrafiltration membrane with a nominal separation limit (cutoff) of from 1000 to 500 000, preferably with a cutoff of from 100 000 to 300 000. The ultrafiltration membrane preferably consists of an organic polymer or an inorganic material, preference being given to membranes made of polysulfones, polyether sulfones or polyamides. The membrane is preferably shaped, as membrane modules, tubular modules, capillary modules, plate modules and spiral coil modules. The ultrafiltration is generally carried out at a transmembrane pressure of from 2 to 10 bar, preferably 3 to 6 bar. The temperature is from 20 to 80° C., preferably 40 to 60° C., in order to reduce the viscosity of the concentrate which increases on accumulation of the thickener polymer during the ultrafiltration.

The liquid obtained after the ultrafiltration comprises essentially glycols and water. After alkalization to pH>7, this glycol/water mixture is subjected to fractional distillation in order to remove the glycols from it.

In a further preferred embodiment, the product of the coarse filtration is alkalized. The amount of alkalis is generally at least 0.1% by weight, based on the product of the coarse filtration. Preference is given to an amount of from 0.3 to 3% by weight, in particular 0.5 to 2% by weight. Suitable alkaline agents are, for example, oxides and hydroxides of alkali metals and alkaline earth metals, such as, for example, calcium oxide, calcium hydroxide, sodium hydroxide or potassium hydroxide. The alkalis can be used in solid form or in solution, preferably aqueous solution. The alkalized used aircraft de-icing agent is then subjected to a first distillation stage in which water is separated off. The above procedure corresponds to process steps (2) and (3) given above.

The bottom of this first distillation stage, which comprises the glycols, is then subjected to a fractional distillation in which the glycols are produced as distillate. For the distillation, the concentrate, optionally after adjusting the pH, is introduced into a distillation receiver, and fractionally distilled over a distillation column. The methods and devices for carrying out this distillation can correspond to those known in the prior art. The reprocessed glycol is obtained as distillate. The distillation bottom is discarded.

The method according to the invention is particularly suitable for used aircraft de-icing agents which comprise, besides water,
(a) 1 to 60% by weight, preferably 5 to 50% by weight, of at least one glycol having 2 or 3 carbon atoms or a diglycol having 4 to 6 carbon atoms, for example ethylene glycol, diethylene glycol, propylene glycol,
(b) up to 0.8% by weight, preferably 0.05 to 0.5% by weight, of the specified water-soluble polymers from the group of polyacrylates and polymethacrylates,
(c) about 0.01 to 1% by weight of the specified surfactants, preferably from the group of anionic surfactants, for example sulfonates such as olefinsulfonates and alkylbenzenesulfonates,
(d) about 0.001 to 0.1% by weight of corrosion inhibitor, preferably from the group of triazoles.

The stated composition refers to the aircraft de-icing agent prior to its use.

The desired quality of the glycols obtained with the method according to the invention is stipulated by the following criteria:
a) a surfactant concentration of less than 100 ppm
b) a water content in accordance with DIN 51 777 of max. 0.5% by weight
c) a glycolic acid content of less than 100 ppm, preferably less than 20 ppm
d) a formic acid content of less than 100 ppm, preferably less than 20 ppm
e) a lactic acid content of less than 100 ppm, preferably less than 20 ppm
f) an acetic acid content of less than 100 ppm, preferably less than 20 ppm
g) a propionic acid content of less than 100 ppm, preferably less than 20 ppm The desired content of glycol esters of the acids specified under c) to g) at most as high as the content of the acids.

The invention claimed is:

1. A method for reprocessing a used aircraft de-icing agent comprising glycol and suspended impurities, wherein the method comprises the steps of:
    (1) separating off the suspended impurities from the used aircraft de-icing agent to form a partially reprocessed used aircraft de-icing agent,
    (2) treating the partially reprocessed used aircraft de-icing agent obtained from step (1) such that any thickeners present therein are no longer capable of gel formation,
    (3) before or after step (2), adjusting to a pH>7 by adding potassium hydroxide,
    (4) followed by fractionally distilling off the glycols.

2. The method as claimed in claim 1, in which the separating off step (1) involves a coarse filtration, and a subsequent ultrafiltration through a membrane.

3. The method as claimed in claim 1, wherein the partially reprocessed used aircraft de-icing agent from step (1) is alkalized and then subjected to a first distillation stage in which water is separated off.

4. The method as claimed in claim 3, wherein the alkalization takes place with at least 0.1% by weight of potassium hydroxide, based on the partially reprocessed used aircraft de-icing agent from step (1).

5. The method as claimed in claim 1, wherein prior to being used to de-ice an airplane, the used aircraft de-icing agent comprises,
    (a) 1 to 60% by weight, of at least one glycol having 2 or 3 carbon atoms or of a diglycol having 4 to 6 carbon atoms,
    (b) up to 0.8% by weight of water-soluble polymers selected from the group consisting of polyacrylates and polymethacrylates,
    (c) 0.01 to 1% by weight of surfactants, and
    (d) 0.001 to 0.1% by weight of corrosion inhibitors, with the remainder being water.

* * * * *